(12) United States Patent
van Zijl et al.

(10) Patent No.: US 8,834,844 B2
(45) Date of Patent: Sep. 16, 2014

(54) CHEMICAL EXCHANGE SATURATION TRANSFER BASED MRI USING REPORTER GENES AND MRI METHODS RELATED THERETO

(75) Inventors: Peter C. M. van Zijl, Ellicott City, MD (US); Assaf A. Gilad, Bethesda, MD (US); Jeff Bulte, Fulton, MD (US); Michael T. Mcmahon, Baltimore, MD (US); Raman Venu, Ellicott City, MD (US); Paul T. Winnard, Jr., Glen Burnie, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/566,785

(22) Filed: Aug. 3, 2012

(65) Prior Publication Data

US 2013/0058874 A1    Mar. 7, 2013

Related U.S. Application Data

(62) Division of application No. 11/883,533, filed as application No. PCT/US2006/004187 on Feb. 7, 2006, now Pat. No. 8,236,572.

(60) Provisional application No. 60/650,746, filed on Feb. 7, 2005.

(51) Int. Cl.
*A61B 5/055* (2006.01)
*A61K 49/14* (2006.01)
*A61B 6/00* (2006.01)

(52) U.S. Cl.
CPC ............... *A61K 49/14* (2013.01); *A61B 5/055* (2013.01); *A61B 6/481* (2013.01)
USPC ............... 424/9.3; 435/6.1; 436/86; 436/173; 600/410

(58) Field of Classification Search
CPC . A61K 49/14; A61K 49/0045; A61K 49/146; C12N 2510/00; C12N 2506/02; C12N 5/0606; C12N 5/0657; C12N 5/069; C12N 5/1138; C12N 15/115; C12N 2310/14; C12N 2310/16; C12N 2310/141; C12N 2310/3519; C12N 2330/51; A61B 5/055
USPC ............. 424/9.3; 436/173; 600/410, 416, 456
See application file for complete search history.

(56) References Cited

PUBLICATIONS

Gilad et al. "MRI reporter gene providing contrast based on chemical exchange saturation transfer (CEST)" http://cds.ismrm.org/ismrm-2005/Files/00363.pdf.*
Louie et al. "In vivo visualization of gene expression using magnetic resonance imaging", Nature Biotechnology, Mar. 2000, v. 18, pp. 321-325.*

(Continued)

*Primary Examiner* — Yelena G Gakh
(74) *Attorney, Agent, or Firm* — Edwards Wildman Palmer LLP; Peter F. Corless; Richard B. Emmons

(57) ABSTRACT

Featured are a new class of reporter genes including reporter compositions as well as methods, MRI systems and MRI imaging kits related thereto. The genes according to the present invention provide MR contrast when the sample/subject is irradiated at a specific off-resonance radio-frequency (RF frequency), where the contrast mechanism utilizes chemical exchange saturation transfer (CEST) technique for imaging.

7 Claims, 7 Drawing Sheets

(56) References Cited

PUBLICATIONS

Goffeney et al. "Sensitive NMR Detection of Cationic-Polymer-Based Gene Delivery Systems Using Saturation Transfer via Proton Exchange" J. Am. Chem. Soc., 2001, v. 123, pp. 8628-8629.*

Hashida et al. "Fusion of HIV-1 Tat protein transduction domain to poly-lysine as a new DNA delivery tool", British J. Cancer, 2004, v. 90, pp. 1252-1258.*

* cited by examiner

SEQUENCE LISTING

```
<160> NUMBER OF SEQ ID NOS: 15

<210> SEQ ID NO 1
<211> LENGTH: 621
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ggtaccgcca ccatgggaag aaggaggcgc cggcggaggc ggcggcgaag acgcaggaga      60
aggaggagga gacgcagacg aagaagaagg agaagacgca gacggcggcg acgacgcaga     120
aggcgaagga ggagaagaag aaggaggagg agacggagac gacggcggag gaggagacgg     180
```

-continued

```
aggcgccggc gcagaaggcg ccggcgcagg aggagacgga ggaggcgaag gaggcgcagg    240
aggaggcgca ggcgacggcg caggcgaagg agaagaagac gaagaaggcg gcggaggcgg    300
cggcggaggc ggagaaggcg acggcgacga cggcgaggat cccgccgacg gcggcgacgc    360
agaagacgcc gcaggaggcg ccggcggaga cgacggcgac gccggcggag gcgacgcagg    420
cgcagaaggc ggaggcgaag aagaaggagg aggcggaggc gccggcggag gcgccggcgg    480
cgacggagaa ggcggaggag acggcggaga agaaggcgga gacgacgccg aagaagaaga    540
cggagacgga gaaggaggag gaggcgacgc aggaggcgaa gaagacgacg ccgcaggcgg    600
cggagaagga ggcggtctag a                                              621
```

```
<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Lys Lys Lys Lys Lys Lys Lys Gly Ser Met Lys Lys Lys Lys Lys
1               5                   10                  15

Lys Lys Lys

<210> SEQ ID NO 3
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(520)
<223> OTHER INFORMATION: This sequence may encompass 1 to 20 "Met Lys
      Lys Lys Lys Lys Lys Lys Lys Lys Lys Lys Lys Lys Lys Lys Lys
      Lys Lys Lys Lys Lys Lys Lys Lys Lys" repeating units

<400> SEQUENCE: 3

Met Lys Lys Lys Lys Lys Lys Lys Lys Lys Lys Lys Lys Lys Lys Lys
1               5                   10                  15

Lys Lys Lys Lys Lys Lys Lys Lys Lys Met Lys Lys Lys Lys Lys Lys
                20                  25                  30

Lys Lys Lys Lys Lys Lys Lys Lys Lys Lys Lys Lys Lys Lys Lys Lys
            35                  40                  45

Lys Lys Lys Lys Met Lys Lys Lys Lys Lys Lys Lys Lys Lys Lys Lys
        50                  55                  60

Lys Lys Lys Lys Lys Lys Lys Lys Lys Lys Lys Lys Lys Lys Met Lys
65                  70                  75                  80

Lys Lys Lys Lys Lys Lys Lys Lys Lys Lys Lys Lys Lys Lys Lys Lys
                85                  90                  95

Lys Lys Lys Lys Lys Lys Met Lys Lys Lys Lys Lys Lys Lys Lys Lys
            100                 105                 110

Lys Lys Lys Lys Lys Lys Lys Lys Lys Lys Lys Lys Lys Lys Lys Lys
        115                 120                 125

Lys Lys Met Lys Lys Lys Lys Lys Lys Lys Lys Lys Lys Lys Lys Lys
    130                 135                 140

Lys Lys Lys Lys Lys Lys Lys Lys Lys Lys Lys Met Lys Lys Lys
145                 150                 155                 160
```

Lys Lys Lys Lys Lys Lys Lys Lys Lys Lys Lys Lys Lys Lys
                165                 170                 175

Lys Lys Lys Lys Lys Lys Met Lys Lys Lys Lys Lys Lys Lys Lys
                180                 185                 190

Lys Lys Lys Lys Lys Lys Lys Lys Lys Lys Lys Lys Lys Lys Lys
                195                 200                 205

Met Lys Lys Lys Lys Lys Lys Lys Lys Lys Lys Lys Lys Lys
210                 215                 220

Lys Lys Lys Lys Lys Lys Lys Lys Met Lys Lys Lys Lys Lys Lys
225                 230                 235                 240

Lys Lys Lys Lys Lys Lys Lys Lys Lys Lys Lys Lys Lys Lys Lys
                245                 250                 255

Lys Lys Lys Lys Met Lys Lys Lys Lys Lys Lys Lys Lys Lys Lys
                260                 265                 270

Lys Lys Lys Lys Lys Lys Lys Lys Lys Lys Lys Lys Lys Met Lys
                275                 280                 285

Lys Lys Lys Lys Lys Lys Lys Lys Lys Lys Lys Lys Lys Lys Lys
                290                 295                 300

Lys Lys Lys Lys Lys Lys Lys Met Lys Lys Lys Lys Lys Lys Lys
305                 310                 315                 320

Lys Lys Lys Lys Lys Lys Lys Lys Lys Lys Lys Lys Lys Lys Lys
                325                 330                 335

Lys Lys Met Lys Lys Lys Lys Lys Lys Lys Lys Lys Lys Lys Lys
                340                 345                 350

Lys Lys Lys Lys Lys Lys Lys Lys Lys Lys Met Lys Lys Lys
                355                 360                 365

Lys Lys Lys Lys Lys Lys Lys Lys Lys Lys Lys Lys Lys Lys Lys
                370                 375                 380

Lys Lys Lys Lys Lys Met Lys Lys Lys Lys Lys Lys Lys Lys Lys
385                 390                 395                 400

Lys Lys Lys Lys Lys Lys Lys Lys Lys Lys Lys Lys Lys Lys Lys
                405                 410                 415

Met Lys Lys Lys Lys Lys Lys Lys Lys Lys Lys Lys Lys Lys
                420                 425                 430

Lys Lys Lys Lys Lys Lys Lys Lys Met Lys Lys Lys Lys
435                 440                 445

Lys Lys Lys Lys Lys Lys Lys Lys Lys Lys Lys Lys Lys Lys Lys
                450                 455                 460

Lys Lys Lys Lys Met Lys Lys Lys Lys Lys Lys Lys Lys Lys Lys
465                 470                 475                 480

Lys Lys Lys Lys Lys Lys Lys Lys Lys Lys Lys Lys Met Lys
                485                 490                 495

Lys Lys Lys Lys Lys Lys Lys Lys Lys Lys Lys Lys Lys Lys
                500                 505                 510

Lys Lys Lys Lys Lys Lys Lys Lys
                515                 520

<210> SEQ ID NO 4
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(208)
<223> OTHER INFORMATION: This sequence may encompass 1 to 8 "Met Lys Lys
      Lys Lys Lys Lys Lys Lys Lys Lys Lys Lys Lys Lys Lys Lys
      Lys Lys Lys Lys Lys Lys Lys" repeating units

<400> SEQUENCE: 4

Met Lys Lys Lys Lys Lys Lys Lys Lys Lys Lys Lys Lys Lys Lys Lys
1               5                   10                  15

Lys Lys Lys Lys Lys Lys Lys Lys Lys Met Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Met Lys Lys Lys Lys Lys Lys Lys Lys Lys Lys
    50                  55                  60

Lys Lys Lys Lys Lys Lys Lys Lys Lys Lys Lys Lys Lys Met Lys
65                  70                  75                  80

Lys Lys Lys Lys Lys Lys Lys Lys Lys Lys Lys Lys Lys Lys Lys
            85                  90                  95

Lys Lys Lys Lys Lys Lys Lys Met Lys Lys Lys Lys Lys Lys Lys
        100                 105                 110

Lys Lys Lys Lys Lys Lys Lys Lys Lys Lys Lys Lys Lys Lys Lys
    115                 120                 125

Lys Lys Met Lys Lys Lys Lys Lys Lys Lys Lys Lys Lys Lys Lys
130                 135                 140

Lys Lys Lys Lys Lys Lys Lys Lys Lys Met Lys Lys Lys Lys Lys
145                 150                 155                 160

Lys Lys Lys Lys Lys Lys Lys Lys Lys Lys Lys Lys Lys Lys Lys
            165                 170                 175

Lys Lys Lys Lys Lys Lys Met Lys Lys Lys Lys Lys Lys Lys Lys
        180                 185                 190

Lys Lys Lys Lys Lys Lys Lys Lys Lys Lys Lys Lys
    195                 200                 205

<210> SEQ ID NO 5
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Lys Lys Lys Lys Lys Lys Lys Lys Lys Lys Lys Lys Lys Lys
1               5                   10                  15

Lys Lys Lys Lys Lys Lys Lys Lys Lys Met Lys Lys Lys Lys Lys
            20                  25                  30

Lys Lys Lys Lys Lys Lys Lys Lys Lys Lys Lys Lys Lys Lys Lys
        35                  40                  45

Lys Lys Lys Lys Met Lys Lys Lys Lys Lys Lys Lys Lys Lys Lys
    50                  55                  60

Lys Lys Lys Lys Lys Lys Lys Lys Lys Lys Lys Lys Lys Met Lys
65                  70                  75                  80

Lys Lys Lys Lys Lys Lys Lys Lys Lys Lys Lys Lys Lys Lys Lys
            85                  90                  95

Lys Lys Lys Lys Lys Lys Lys Met Lys Lys Lys Lys Lys Lys Lys
        100                 105                 110

Lys Lys Lys Lys Lys Lys Lys Lys Lys Lys Lys Lys Lys Lys Lys

```
                115                 120                 125
Lys Lys Met Lys Lys Lys Lys Lys Lys Lys Lys Lys Lys Lys
        130                 135                 140
Lys Lys Lys Lys Lys Lys Lys Lys Lys Lys Met Lys Lys Lys
145                 150                 155                 160
Lys Lys Lys Lys Lys Lys Lys Lys Lys Lys Lys Lys Lys Lys
                165                 170                 175
Lys Lys Lys Lys Lys Lys Met Lys Lys Lys Lys Lys Lys Lys
            180                 185                 190
Lys Lys Lys Lys Lys Lys Lys Lys Lys Lys Lys Lys Lys
            195                 200                 205

<210> SEQ ID NO 6
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(280)
<223> OTHER INFORMATION: This sequence may encompass 1 to 10 "Met Lys
      Lys Lys Lys Lys Lys Lys Lys Lys Lys Lys Lys Lys Lys Lys Lys
      Lys Lys Lys Lys Lys Lys Lys Lys Gly Ser" repeating units

<400> SEQUENCE: 6

Met Lys Lys Lys Lys Lys Lys Lys Lys Lys Lys Lys Lys Lys
1               5                   10                  15
Lys Lys Lys Lys Lys Lys Lys Lys Lys Gly Ser Met Lys Lys Lys
            20                  25                  30
Lys Lys Lys Lys Lys Lys Lys Lys Lys Lys Lys Lys Lys
            35                  40                  45
Lys Lys Lys Lys Lys Lys Gly Ser Met Lys Lys Lys Lys Lys
            50                  55                  60
Lys Lys Lys Lys Lys Lys Lys Lys Lys Lys Lys Lys Lys Lys
65                  70                  75                  80
Lys Lys Gly Ser Met Lys Lys Lys Lys Lys Lys Lys Lys Lys
                85                  90                  95
Lys Lys Lys Lys Lys Lys Lys Lys Lys Lys Lys Lys Gly Ser
            100                 105                 110
Met Lys Lys Lys Lys Lys Lys Lys Lys Lys Lys Lys
        115                 120                 125
Lys Lys Lys Lys Lys Lys Lys Lys Gly Ser Met Lys Lys Lys
        130                 135                 140
Lys Lys Lys Lys Lys Lys Lys Lys Lys Lys Lys Lys Lys Lys
145                 150                 155                 160
Lys Lys Lys Lys Lys Lys Gly Ser Met Lys Lys Lys Lys Lys
                165                 170                 175
Lys Lys Lys Lys Lys Lys Lys Lys Lys Lys Lys Lys Lys
            180                 185                 190
Lys Lys Gly Ser Met Lys Lys Lys Lys Lys Lys Lys Lys Lys
            195                 200                 205
Lys Lys Lys Lys Lys Lys Lys Lys Lys Lys Lys Lys Gly Ser
        210                 215                 220
Met Lys Lys Lys Lys Lys Lys Lys Lys Lys Lys Lys Lys Lys
225                 230                 235                 240
```

```
Lys Lys Lys Lys Lys Lys Lys Lys Gly Ser Met Lys Lys Lys
                    245                 250             255

Lys Lys Lys Lys Lys Lys Lys Lys Lys Lys Lys Lys Lys Lys
            260                 265             270

Lys Lys Lys Lys Lys Lys Gly Ser
        275             280

<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Lys Lys Lys Lys Lys Lys Lys Lys Lys Lys Lys Lys Lys
1               5                   10                  15

Lys Lys Lys Lys Lys Lys Lys Lys Lys Lys
            20                  25

<210> SEQ ID NO 8
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Lys Lys Lys Lys Lys Lys Lys Lys Lys Lys Lys Lys
1               5                   10                  15

Lys Lys Lys Lys Lys Lys Lys Lys Lys Met Lys Lys Lys Lys
            20                  25              30

Lys Lys Lys Lys Lys Lys Lys Lys Lys Lys Lys Lys Lys Lys
        35                  40              45

Lys Lys Lys Lys
    50

<210> SEQ ID NO 9
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Lys Lys Lys Lys Lys Lys Lys Lys Lys Lys Lys Lys Lys
1               5                   10                  15

Lys Lys Lys Lys Lys Lys Lys Lys Met Lys Lys Lys Lys
            20                  25              30

Lys Lys Lys Lys Lys Lys Lys Lys Lys Lys Lys Lys Lys Lys
        35                  40              45

Lys Lys Lys Lys Met Lys Lys Lys Lys Lys Lys Lys Lys
    50              55                  60

Lys Lys Lys Lys Lys Lys Lys Lys Lys Lys Lys
65                  70                  75

<210> SEQ ID NO 10
<211> LENGTH: 104
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 10

Met Lys Lys Lys Lys Lys Lys Lys Lys Lys Lys Lys Lys Lys Lys
1               5                   10                  15

Lys Lys Lys Lys Lys Lys Lys Lys Lys Met Lys Lys Lys Lys
            20                  25                  30

Lys Lys Lys Lys Lys Lys Lys Lys Lys Lys Lys Lys
        35                  40                  45

Lys Lys Lys Lys Met Lys Lys Lys Lys Lys Lys Lys Lys
    50                  55                  60

Lys Lys Lys Lys Lys Lys Lys Lys Lys Lys Met Lys
65                  70                  75              80

Lys Lys Lys Lys Lys Lys Lys Lys Lys Lys Lys Lys
            85                  90                  95

Lys Lys Lys Lys Lys Lys Lys
            100

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Lys Lys Lys Lys Lys Lys Lys Lys Lys Lys Lys Lys Lys Lys
1               5                   10                  15

Lys Lys Lys Lys Lys Lys Lys Lys Lys Lys Gly Ser
            20                  25

<210> SEQ ID NO 12
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Lys Lys Lys Lys Lys Lys Lys Lys Lys Lys Lys Lys Lys Lys
1               5                   10                  15

Lys Lys Lys Lys Lys Lys Lys Lys Gly Ser Met Lys Lys
            20                  25              30

Lys Lys Lys Lys Lys Lys Lys Lys Lys Lys Lys Lys Lys Lys
        35                  40                  45

Lys Lys Lys Lys Lys Lys Gly Ser
    50                  55

<210> SEQ ID NO 13
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

Met Lys Lys Lys Lys Lys Lys Lys Lys Lys Lys Lys Lys Lys Lys
1               5                   10                  15

Lys Lys Lys Lys Lys Lys Lys Lys Lys Gly Ser Met Lys Lys Lys
            20                  25              30

Lys Lys Lys Lys Lys Lys Lys Lys Lys Lys Lys Lys Lys Lys Lys
        35                  40                  45

Lys Lys Lys Lys Lys Gly Ser Met Lys Lys Lys Lys Lys Lys Lys
    50                  55              60

Lys Lys Lys Lys Lys Lys Lys Lys Lys Lys Lys Lys Lys Lys Lys
65                  70                  75                  80

Lys Lys Gly Ser

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Lys Lys Lys Lys Lys Lys Lys Lys Lys Lys Lys Lys Lys Lys
1               5                   10                  15

Lys Lys Lys Lys Lys Lys Lys Lys Lys Gly Ser Met Lys Lys Lys
            20                  25              30

Lys Lys Lys Lys Lys Lys Lys Lys Lys Lys Lys Lys Lys Lys Lys
        35                  40                  45

Lys Lys Lys Lys Lys Gly Ser Met Lys Lys Lys Lys Lys Lys Lys
    50                  55              60

Lys Lys Lys Lys Lys Lys Lys Lys Lys Lys Lys Lys Lys Lys Lys
65                  70                  75                  80

Lys Lys Gly Ser Met Lys Lys Lys Lys Lys Lys Lys Lys Lys Lys
            85                  90                  95

Lys Lys Lys Lys Lys Lys Lys Lys Lys Lys Lys Lys Lys Gly Ser
        100                 105                 110

<210> SEQ ID NO 15
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Lys Lys Lys Lys Lys Lys Lys Lys Lys Lys Lys Lys Lys Lys
1               5                   10                  15

Lys Lys Lys Lys Lys Lys Lys Lys Lys Gly Ser Met Lys Lys Lys
            20                  25              30

Lys Lys Lys Lys Lys Lys Lys Lys Lys Lys Lys Lys Lys Lys Lys
        35                  40                  45

Lys Lys Lys Lys Lys Gly Ser Met Lys Lys Lys Lys Lys Lys Lys
    50                  55              60

Lys Lys Lys Lys Lys Lys Lys Lys Lys Lys Lys Lys Lys Lys Lys
65                  70                  75                  80

Lys Lys Gly Ser Met Lys Lys Lys Lys Lys Lys Lys Lys Lys Lys
            85                  90                  95

Lys Lys Lys Lys Lys Lys Lys Lys Lys Lys Lys Lys Lys Gly Ser

|           |           | 100       |           |           | 105       |           |           | 110       |           |           |
|-----------|-----------|-----------|-----------|-----------|-----------|-----------|-----------|-----------|-----------|-----------|

Met Lys Lys Lys Lys Lys Lys Lys Lys Lys Lys Lys Lys Lys Lys
    115                  120                125

Lys Lys Lys Lys Lys Lys Lys Lys Lys Gly Ser Met Lys Lys Lys
    130                  135          140

Lys Lys Lys Lys Lys Lys Lys Lys Lys Lys Lys Lys Lys Lys Lys
145                150                155                160

Lys Lys Lys Lys Lys Lys Gly Ser Met Lys Lys Lys Lys Lys Lys
            165              170                175

Lys Lys Lys Lys Lys Lys Lys Lys Lys Lys Lys Lys Lys Lys Lys
    180                  185                190

Lys Lys Gly Ser Met Lys Lys Lys Lys Lys Lys Lys Lys Lys Lys
      195                200              205

Lys Lys Lys Lys Lys Lys Lys Lys Lys Lys Lys Lys Lys Gly Ser
    210                  215                220

CHEMICAL EXCHANGE SATURATION TRANSFER BASED MRI USING REPORTER GENES AND MRI METHODS RELATED THERETO

This application is a divisional of U.S. patent application Ser. No. 11/883,833, filed May 16, 2008 now U.S. Pat. No. 8,236,572 which is a 371 National Stage application of PCT/US06/004187, filed Feb. 7, 2006, which claims the benefit of U.S. Provisional Application Ser. No. 60/650,746, filed Feb. 7, 2005. Each of the aforementioned patent applications is hereby incorporated by reference in its entirety.

STATEMENT REGARDING FEDERALLY-SPONSORED RESEARCH

The present invention was supported by grants from the National Institute of Health (NIH), grant number NS 045062 and P50CA103175. The U.S. Government may have certain rights to the present invention.

FIELD OF INVENTION

The present invention generally relates to methods of magnetic resonance imaging (MRI), more particularly MRI that is based on chemical exchange saturation transfer (CEST) and more specifically CEST based MRI that utilize reporter genes as a contrast agent.

BACKGROUND OF THE INVENTION

The transplantation or transfusion of therapeutic cells has been pursued as very actively by researchers over the last decade, and, for progenitor and stem cell therapy, remarkable progress has been made in animal disease models. There are several imaging modalities that are capable of non-invasively and repetitively imaging targeted cells and cellular processes in living organisms. Such imaging modalities include γ-camera imaging, single photon emission computed tomography (SPECT), and positron emission tomography or PET (which use radioactive labels), bioluminescence imaging, and MR imaging. When these modalities are compared, however, only MR imaging offers near-cellular spatial resolution, with the potential of imaging only a few cells.

MR imaging, γ-camera imaging, and SPECT do require tagging of the cells with a suitable marker, while reporter genes have been developed for bioluminescent and PET imaging (although PET can also use tagged cells[1]). As for PET imaging, studies by Gelovani aka Tjuvajev and others have shown that HSV-tk can be used [Tjuvajev, J. G. et al. Noninvasive imaging of herpes virus thymidine kinase gene transfer and expression: a potential method for monitoring clinical gene therapy. *Cancer Res* 56, 4087-4095 (1996); Tjuvajev, J. G. et al. Imaging the expression of transfected genes in vivo. *Cancer Res* 55, 6126-6132 (1995); and Gambhir, S. S. et al. Imaging adenoviral-directed reporter gene expression in living animals with positron emission tomography. *Proc Natl Acad Sci USA* 96, 2333-2338 (1999)]. The dopamine type 2 receptor, the somatostatin receptor type 2, and the bombesin receptor systems have also been used as potential nuclear imaging probes of gene expression, although to lesser extents [Gambhir, S. S. et al. Imaging adenoviral-directed reporter gene expression in living animals with positron emission tomography. *Proc Natl Acad Sci USA* 96, 2333-2338 (1999) and Rogers, B. E. et al. Localization of iodine-125-mIP-Des-Met14-bombesin (7-13)NH2 in ovarian carcinoma induced to express the gastrin releasing peptide receptor by adenoviral vector-mediated gene transfer. *J Nucl Med* 38, 1221-1229 (1997)]. In the context of cellular imaging, the HSV1-tk reporter system has been used to image intracellular pathways, such as the induction of p53 expression and T-cell activation [Ponomarev, V. et al. Imaging TCR-dependent NFAT-mediated T-cell activation with positron emission tomography in vivo. *Neoplasia* 3, 480-488 (2001)], and is currently being explored for imaging of stem cell [Ivanova, A. et al. Imaging adoptive stem cell therapy with HSV-tk/GFP reporter gene. *Mol Imaging* 1, 208-209 (2002)] and T cell trafficking [Koehn, G. et al. Serial in vivo imaging of the targeted migration of human HSV-TK-transduced antigen-specific lymphocytes. *Nat Biotechnol* 21, 405-413 (2003) and Dubey, P. et al. Quantitative imaging of the T cell antitumor response by positron-emission tomography. *Proc Natl Acad Sci USA* 100, 1232-1237 (2003)].

For bioluminescent imaging, firefly luciferase is commonly used, but other enzymes, i.e., *Renilla* luciferase, have been developed as well [Bhaumik, S. & Gambhir, S. S. Optical imaging of *Renilla* luciferase reporter gene expression in living mice. *Proc Nail Acad Sci USA* 99, 377-382 (2002)]. The reporter genes have been successfully used for the detection of homing sites of prokaryotes [Hardy, J. et al. Extracellular replication of *Listeria* monocytogenes in the murine gall bladder. *Science* 303, 851-853 (2004)] and viruses [Luker, G. D. et al. Noninvasive bioluminescence imaging of herpes simplex virus type 1 infection and therapy in living mice. *J Virol* 76, 12149-12161 (2002)]. As for imaging of eukaryote cells, transfected islet cell grafts have been followed without adverse effects on islet function [Lu, Y. et al. Bioluminescent monitoring of islet graft survival after transplantation. *Mol Ther* 9, 428-435 (2004), and trafficking/migration of C17.2 cells has been successfully visualized in animal model of stroke and intracranial gliomas. Similarly, lymphocyte trafficking has been monitored serially over time.

The reporter gene strategy is so sensitive that even single hematopoietic bone marrow stem cells can be detected following transfusion and replication in the host (Contag, SMI 2003). Recently, cells have also been transfected with double or triple reporter genes, allowing the application of multiple imaging modalities. A hallmark for the use of these reporter genes in both PET and bioluminescent imaging is that they require the administration of a substrate, i.e., luciferin, coelenterazine, FIAU, or FHBG. The use of reporter genes has a narrow time window of imaging, unless repeated injections of substrate are applied, and some agents are unable to cross an intact blood-brain barrier. An example of an endogenous reporter gene that does not require substrate administration is green fluorescent protein (EGFP). However, so far, optical imaging cannot be used in larger animals such as mammals.

For the cells of interest to be visualized using MR imaging, they need to be magnetically labeled in order to be discriminated from the surrounding native tissue. For both applications, gadolinium chelates may be used, but these agents exhibit low relaxivities, which further decrease upon cellular internalization. Furthermore, gadolinium is not biocompatible, and very little is known about its potential toxicity following cellular dechelation over time. Because of their biocompatibility and strong effects on T2 and T2* relaxation, superparamagnetic iron oxides (SPIO) are now the preferred magnetic label for use in MR cell tracking. As they are composed of thousands of iron atoms, they defeat the inherent low contrast agent sensitivity of MRI. They also have other convenient properties, including the ability to be detected by light (Prussian Blue stain) and electron microscopy, and the ability to change their magnetic properties according to size, with the potential to reveal their structural (bound) conformation.

Despite these recent advances, there are several limitations that hamper exploiting the full potential of high-resolution MRI cell tracking using iron oxide particles. The amounts of iron necessary for sufficient detection are in the picogram range per cell. Few detailed studies on the potential adverse effect of iron on normal cellular function have been performed. As iron plays a role in many metabolic pathways, it would not be surprising to encounter negative effects in labeled cells that are not "professional scavengers or biodegraders" (i.e., not macrophages). Indeed, while Feridex labeling of human mesenchymal stem cells was found not to affect viability or proliferation, it has been found that the differentiation of mesenchymal stem cells (MSCs) into chondrocytes was markedly inhibited [Bulte, J. W. M., Kraitchman, D. L., Mackay, A. M. & Pittenger, M. F. Chondrogenic differentiation of mesenchymal stem cells is inhibited after magnetic labeling with ferumoxides. *Blood* 104 (2004), while adipogenic and osteogenic differentiation were not affected. The unexpected inhibition of the mesenchymal pathway into chondrogenic differentiation was mediated by the Feridex and not the PLL, through an as yet unknown mechanism. These results highlight the need for caution in the use of Feridex-labeling for certain cell tracking applications.

More generally, a potential limitation of SPIO-based cell tracking lies in the fact that any non-genetic material carried by the cell is eventually degraded, can exit the cell, or be incorporated into neighboring cells following cell death. It is thus unclear how long after labeling cells can be visualized and monitored reliably. Moreover, fast proliferating, dividing cells can rapidly dilute the iron label by cell division. As the effective concentration of these contrast materials is reduced with every cell division, the detection efficiency also is reduced. To date, all MR cell tracking approaches and genetically encoded MR reporters utilize the same contrast mechanism, (super)paramagnetic relaxation enhancement, allowing detection of only one type of labelled cell.

When reviewing the available MR literature, it is clear that the development of a suitable reporter gene for MR imaging has long been an elusive goal. Early attempts have used creatine kinase and cytosine deaminase [Koretsky, A. P., Brosnan, M. J., Chen, L. H., Chen, J. D. & Van Dyke, T. NMR detection of creatine kinase expressed in liver of transgenic mice: determination of free ADP levels. *Proc Natl Acad Sci USA* 87, 3112-3116 (1990) and Stegman, L. D. et al. Noninvasive quantitation of cytosine deaminase transgene expression in human tumor xenografts with in vivo magnetic resonance spectroscopy. *Proc Natl Acad Sci USA* 96, 9821-9826 (1999)] for spectroscopic imaging but, again, these encode for enzymes that convert substrates (adenine diphosphate and 5-fluorocytosine, respectively). Meade et al. have used the lacZ gene encoding for β-galactosidase and shown that embryonic cells injected with eGad can be selectively visualized [Louie, A. Y. et al. In vivo visualization of gene expression using magnetic resonance imaging. *Nat Biotechnol* 18, 321-325 (2000)]. LacZ-transfected cells have recently also been used to convert the NMR-sensitive molecule, 4-fluoro-2-nitrophenyl-β-D-galactopyranoside [Cui, W. et al. Novel NMR approach to assessing gene transfection: 4-fluoro-2-nitrophenyl-beta-D-galactopyranoside as a prototype reporter molecule for beta-galactosidase. *Magn Reson Med* 51, 616-620 (2004)]. Use of ferritin as an MR reporter gene has been recently reported [Cohen, B., Dafni, H., Meir, G., Harmelin, A. & Neeman, M. Ferritin as an endogenous MRI reporter for noninvasive imaging of gene expression in C6 glioma tumors. *Neoplasia* 7, 109-117 (2005); Genove, G., Demarco, U., Xu, H., Goins, W. F. & Ahrens, E. T. A new transgene reporter for in vivo magnetic resonance imaging. *Nat Med* (2005)]. Weissleder and Basilion et al. were able to detect transferrin-receptor-overexpressing tumors using a superparamagnetic transferrin probe [Weissleder, R. et al. In vivo magnetic resonance imaging of transgene expression. *Nat Med* 6, 351-355 (2000)].

Chemical exchange saturation transfer (CEST) MR imaging, which is shown schematically in FIG. 1, is a relatively new technique in which low-concentration marker molecules are labeled by saturating their exchangeable protons (e.g., hydroxyl, amine, amide, or imino protons) by radio-frequency (RF) irradiation. If such saturation can be achieved rapidly (i.e., before the proton exchanges), exchange of such labeled protons with water leads to progressive water saturation, allowing indirect detection of the solute via the water resonance through a decrease in signal intensity in MRI [Ward, K. M., Aletras, A. H. & Balaban, R. S. A new class of contrast agents for MRI based on proton chemical exchange dependent saturation transfer (CEST). *J Magn Reson* 143, 79-87 (2000)]. Each CEST contrast agent can have a different saturation frequency, which depends on the chemical shift of the exchangeable proton. The magnitude of proton transfer enhancement (PTE) due to this effect, and the resulting signal reduction from equilibrium ($S_0$) to saturated (S), are given by [Goffeney, N., Bulte, J. W., Duyn, J., Bryant, L. H., Jr. & van Zijl, P. C. Sensitive NMR detection of cationic-polymer-based gene delivery systems using saturation transfer via proton exchange. *J Am Chem Soc* 123, 8628-8629 (2001)]:

$$PTE = \frac{N M_w \alpha k_{ex}}{(1-x_{CA})R_{1wat} + x_{CA}k_{ex}} \cdot \{1 - e^{-[(1-x_{CA})R_{1wat} + x_{CA}k_{ex}]t_{sat}}\}, \quad [\text{Eq. 1}]$$

and $$(1 - S_{sat}/S_0) = \frac{PTE \cdot [CA]}{2 \cdot [H_2O]}. \quad [\text{Eq. 2}]$$

"CA" is the contrast agent containing multiple exchangeable protons, $x_{CA}$ its fractional exchangeable proton concentration, $\alpha$ the saturation efficiency, k the pseudo first-order rate constant, N the number of exchangeable protons per molecular weight unit, and $M_w$ the molecular weight of the CA. The exponential term describes the effect of back exchange and water longitudinal relaxation ($R_{1wat}=1/T_{1wat}$) on the transfer during the RF saturation period ($t_{sat}$). This effect will be bigger when protons exchange faster, but the catch is that saturation must occur faster as well, which increases the radio-frequency power needed. In addition, the resonance of the particular protons must be well separated from water in the proton NMR spectrum (so that it can be irradiated selectively as illustrated in FIG. 1), which requires a slow exchange on the NMR time scale. This condition means that the frequency difference of the exchangeable protons with water is much larger than the exchange rate ($\Delta\omega > k$). Thus, the CEST technology becomes more applicable at higher magnetic fields or when using paramagnetic shift agents [Zhang, S., Merritt, M., Woessner, D. E., Lenkinski, R. E. & Sherry, A. D. PARACEST agents: modulating MRI contrast via water proton exchange. *Acc Chem Res* 36, 783-790 (2003)]. Any molecule that exhibits a significant PTE effect can be classified as a CEST (contrast) agent. The concept of these agents as MR contrast agents is somewhat similar to the chemical amplification of colorimetric labels in in situ gene expression assays. CEST agents can be detected by monitoring the water intensity as a function of the saturation frequency, leading to a so-called z-spectrum. In such spectra, the saturation effect of the contrast agent on the water resonance is displayed as a function of irradiation frequency. The water signal resonates at 4.7 ppm, which therefore shows complete direct saturation. When a sample (or tissue) contains exchangeable protons that have a separate MRI frequency (e.g., amide backbone protons at 8.3 ppm in peptides), their irradiation reduces the water signal.

CEST agents with two types of exchangeable protons that have different chemical shifts can be used to monitor pH based on ratiometric methods. In addition, Sherry et al. and Aime et al. have developed a new class of CEST agents containing a paramagnetic center, so-called PARACEST agents. In this type of agent, a lanthanide ion with a chelator binds water weakly, which can then exchange with bulk water. The bound water has a greater chemical shift than bulk water due to the paramagnetic lanthanide, and can "hop" between free and bound at a fast rate. In addition, Sherry et al. have characterized a series of complexes that have a wide range of exchange rates suitable for large contrasts. PARACEST agents, however, provide contrast only at millimolar concentrations.

In order to effectively develop cell-based therapies that will be applicable in the clinic, noninvasive cellular imaging techniques are required. These imaging techniques are needed to provide detailed information on the biokinetics of administered cells (either transplanted or transfused), and cell-tissue interactions, including preferred pathways of migration, and cell survival. In addition, within the hematological and immunological communities. There also is now increasing interest in obtaining a deeper understanding of the spatiotemporal dynamics of cell "homing" following intravenous injection of hematopoietic and white blood cells.

The references discussed herein are provided solely for their disclosure prior to the filing date of the present application. Nothing herein is to be construed as an admission that the inventors are not entitled to antedate such disclosure by virtue of prior invention.

It thus would be desirable to provide a new reporter gene that can be detected by CEST MR imaging with high sensitivity, and that does not require the administration of exogenous probes or substrates. It also would be particularly desirable to provide methods for making such a reporter gene as well as CEST based MRI methods the embody the use of such reporter genes.

SUMMARY OF THE INVENTION

The present invention features a new class of reporter genes and methods for using such reporter genes for MR imaging. The genes according to the present invention provide MR contrast when the sample/subject is irradiated at a specific off-resonance radio-frequency (RF frequency), where the contrast mechanism utilizes chemical exchange saturation transfer (CEST) technique for imaging.

In particular embodiments, the reporter gene is an artificial protein that is cloned so as to be selectively rich in one amino acid and in specific embodiments, there is cloned and expressed in mammalian cells an artificial protein that is one of a lysine-rich-protein (LRP) or an argenine-rich-protein (ARP). Such different proteins are excitable by different radio frequencies such a CEST reporter system or methodology allows for double or more labeling and detection strategies.

In further embodiments, such artificial genes are integrated into an expression vector (e.g., plasmids, viruses) and can be used as a reporter for gene delivery into cells such as by transfection or infection. It is contemplated, and thus within the scope of the present invention that such reporter genes can be delivered together with therapeutic genes of interest in gene therapy and then be used to assess the efficacy of the gene transfer and treatment and for imaging the transfected tissue areas. It also is contemplated and thus within the scope of the present invention that the biodistribution and sites of natural homing following local or systemic infection can be studied using such transfected bacteria, viruses and parasites.

In one aspect, provided herein are reporter compositions comprising a lysine rich protein (LRP) and a therapeutically effective carrier. In one embodiment, the (LRP) comprises from between about 50 to about 250 lysines. In another embodiment, the reporter composition is functional under normal physiological conditions. In a further embodiment, normal physiological conditions comprise a pH from between about 6.8 to about 7.5. In one embodiment, the reporter composition is not functional under ischemic or apoptotic conditions.

In one aspect, provided herein are reporter compositions comprising an argenine rich protein and a therapeutically effective carrier. In one embodiment, comprising SEQ ID NO.: 1 or a fragment or variant thereof. In another embodiment, the SEQ ID NO.: 1 or a fragment or variant thereof is contained in a vector. In a further embodiment, the vector is one or more of pIRES2-EGFP or pEF1alpha Myc/HIS.

In one aspect, provided herein are reporter compositions comprising a protein rich in amide protons. In one embodiment, the amide protons have a high exchange rate. In another embodiment, the exchange rate is from between about $100^{-1}$ s and about $700^{-1}$ s. In a further embodiment, the exchange rate is from between about $450^{-1}$ s to about $650^{-1}$ s. In one embodiment, the exchange rate is from between about $490^{-1}$ s to about $600^{-1}$ s.

In one aspect, provided herein are reporter compositions comprising a polynucleotide encoding a LRP. In one embodiment, the polynucleotide is contained in an expression vector. In another embodiment, the expression vector comprises an IRES regulator. In another embodiment, the vector is one or more of pIRES2-EGFP or pEF1alpha Myc/HIS. In another embodiment, the polynucleotide comprises $(Met(Lys)_{25})_{1-20}$ (SEQ ID NO: 3) or a fragment or variant thereof. In one embodiment, the polynucleotide comprises $(Met(Lys)_{25})_{1-8}$ (SEQ ID NO: 4) or a fragment or variant thereof. In a further embodiment, the polynucleotide comprises $(Met(Lys)_{25})_8$ (SEQ ID NO: 5) or a fragment or variant thereof. In one embodiment, the polynucleotide comprises $(Met(Lys)_{25}Gly-Ser)_{1-10}$ (SEQ ID NO: 6) or a fragment or variant thereof.

Such CEST reporters advantageously can be applied to label and track the biodistribution and migration of mammalian cells, including hematopetic cells, stem cells, and tumor cells. Such CEST reporters will provide a mechanism for non-invasive repetitive monitoring with 3-D whole body imaging without dependence on light penetration to the region or area of interest.

Also, and unlike conventional reporter genes in PET and bioluminescent imaging, the CEST reporter gene(s) of the present invention is an endogenous reporter that does not require the administration of a substrate and thus obviating the need of substrate-tissue penetration including crossing of the blood-brain barrier. Also, and as compared to conventional MR labeling techniques using contrast agents, the CEST reporters of the present invention will allow for continued monitoring of rapidly dividing cells and also no foreseen confounding artifacts when the cells die. In other words the CEST reporter genes of the present invention allow for discrimination of the live and dead cells. Such CEST reporter genes can be used for MR imaging in connection with a wide range of clinical or diagnostic procedures including, but not limited to, evaluating the efficacy of gene therapy and the monitoring of cell therapy.

In another aspect, provided herein are kits for MRI imaging comprising one or more of a vector expressing and LRP, a vector expressing and ARP, an LRP polypeptide, an APR polypeptide, and instructions for use.

Also featured are MR imaging methods that embody the use of such CEST reporter genes.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 3A is a schematic view illustrating frequency-selective radiofrequency pulses being applied to saturate amide protons that exchange with water protons, thereby reducing the water (MRI) signal intensity ($\Delta$=SI change). FIG. 3B, illustrate immunofluorescent staining of LRP expression in rat 9L-glioma cells. Polyclonal-antibody staining against LRP (red) and nuclear staining (blue). Only cells expressing LRP show intense cytoplasmic LRP staining (FIG. 3B), while control cells (FIG. 3C) show very little or no staining, mainly non-specific around the nuclei. Scale bar: 100 µm. FIG. 3D is a graphical view of absorbance versus number of cells of an MTS assay for mitochondrial metabolic rates (mean±SD) shows no inhibitory effect of LRP on cell metabolism/proliferation (where ● LRP-expressing cells, ○ control EGFP-expressing cells).

FIG. 4A is a phantom layout: PLL, 30 kDa, 100 µM (1) and 10 µM (2); protein extracts from LRP cells (3), control cells (4), and PBS (5); FIG. 4B is a reference image acquired at $\Delta\omega$-3.758 ppm from the water resonance; FIG. 4C is a SI difference map between RF irradiation at $\Delta\omega\pm3.758$ ppm, superimposed on reference image. Pixels outside capillaries were excluded; and FIG. 4D is a t-test map comparing saturation frequencies $\Delta\omega\pm3.758$ ppm (only pixels with P<0.05 are color-coded). Scale bar, 1 mm.

DESCRIPTION OF THE PREFERRED EMBODIMENT

Figure 1:
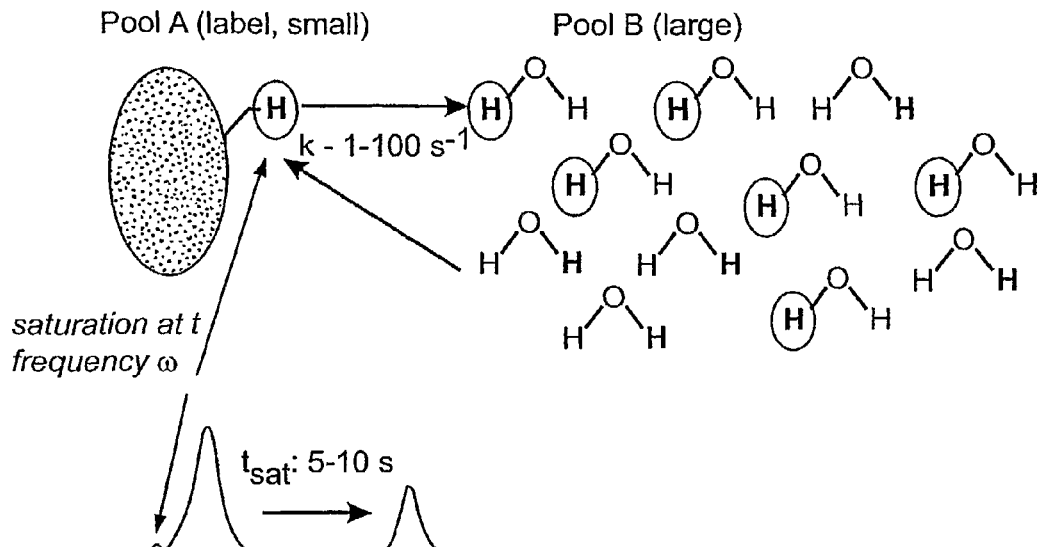
FIG. 1 is a schematic illustration of the principle of chemical exchange saturation transfer (CEST). Protons in a small pool (proton label) of molecules, e.g., amide groups, are saturated and exchange (rate k) with the larger water pool, which provides an unsaturated proton back. Because the unsaturated pool is much larger, there is limited back exchange of saturated protons and the process leads to progressive decay in the water signal, enabling detection of low concentrations. Each amide proton can transfer energy into hundreds or thousands of water protons, depending on the exchange rate. The change in the water signal intensity can be calculated from the difference between saturation at $\pm\Delta\omega$ in 1-D spectra, and these principles form the basis for contrast in MR imaging.

The present invention utilizes the basic capability of cells to over-express polypeptides to design endogenous non-paramagnetic MRI reporter genes, whereby tissue or cell contrast can be achieved using the so-called CEST technique of MRI imaging. Such MRI reporter genes of the present invention are generally characterized as being switchable (i.e., they can be turned on and turned off by selectively applying RF irradiation at the exchangeable proton resonance frequency) and providing contrast after application of an off-resonance saturation RF pulse. This will not interfere with other high resolution MR imaging pulse sequences. In addition, the different reporter genes are such as not to interfere with one another as well.

In the CEST technique, selective RF saturation of the amide protons embodied in the endogenous MRI reporter genes is transferred to the water protons via exchange. Such MRI reporter genes include those which are lysine or argenine rich proteins (LRP or ARP) as more particularly described hereinafter. Also, such contrast is provided by live cells and is not expected to be diluted following cell proliferation as is seen with conventional contrast agents that include (super)paramagnetic material. In sum, the present invention yields reporter genes that are suitable for tracking cells by MRI without the need for a metal or exogenous substrate as would be the case with conventional techniques.

In one aspect, presented herein are reporter compositions comprising a lysine rich protein (LRP) and a therapeutically effective carrier. LRPs may, for example, comprise from between about 50 to about 250 lysines; from between about 70 to about 200 lysines; from between about 100 to about 150 lysines or a number of lysines to provide a sufficient number of amide protons. Exemplary polypeptides comprise, for example, $(Met(Lys)_{25})_{1-20}$ (SEQ ID NO: 3); $(Met(Lys)_{25})_{1-8}$ (SEQ ID NO: 4); $(Met(Lys)_{25})_8$ (SEQ ID NO: 5); $(Met(Lys)_{25}GlySer)_{1-10}$ (SEQ ID NO: 6); $(Met(Lys)_{25})_1$ (SEQ ID NO: 7); $(Met(Lys)_{25})_2$ (SEQ ID NO: 8); $(Met(Lys)_{25})_3$ (SEQ ID NO: 9); $(Met(Lys)_{25})_4$ (SEQ ID NO: 10); $(Met(Lys)_{25}GlySer)_1$ (SEQ ID NO: 11); $(Met(Lys)_{25}GlySer)_2$ (SEQ ID NO: 12); $(Met(Lys)_{25}GlySer)_3$ (SEQ ID NO: 13); $(Met(Lys)_{25}GlySer)_4$ (SEQ ID NO: 14); and/or $(Met(Lys)_{25}GlySer)_8$ (SEQ ID NO: 15).

A reporter composition comprising an argenine rich protein (ARP) and a therapeutically effective carrier. ARPs may, for example, comprise from between about 50 to about 250 argenines; from between about 70 to about 200 argenines; from between about 100 to about 150 argenines or a number of argenines to provide a sufficient number of amide protons. ARPs may comprising SEQ ID NO.: 1 or a fragment or variant thereof.

SEQ ID NO.: 1:
GGTACCGCCACCATGGGAAGAAGGAGGCGCCGGCGGAGGCGGCGGCGAA

GACGCAGGAGAAGGAGGAGGAGACGCAGACGAAGAAGAAGGAGAAGAC

GCAGACGGCGGCGACGACGCAGAAGGCGAAGGAGGAGAAGAAGAAGGA

GGAGGAGACGGAGACGACGGCGGAGGAGGAGACGGAGGCGCCGGCGCA

GAAGGCGCCGGCGCAGGAGGAGACGGAGGAGGCGAAGGAGGCGCAGGA

GGAGGCGCAGGCGACGGCGCAGGCGAAGGAGAAGAAGACGAAGAAGGC

GGCGGAGGCGGCGGCGGAGGCGGAGAAGGCGACGGCGACGACGGCGAgg atccCGCCGACGGCGGCGACGCAGAAGACGCCGCAGGAGGCGCCGGCGGA

GACGACGGCGACGCCGGCGGAGGCGACGCAGGCGCAGAAGGCGGAGGCG

AAGAAGAAGGAGGAGGCGGAGGCGCCGGCGGAGGCGCCGGCGGCGACG

GAGAAGGCGGAGGAGACGGCGGAGAAGAAGGCGGAGACGACGCCGAAG

AAGAAGACGGAGACGGAGAAGGAGGAGGAGGCGACGCAGGAGGCGAAG

AAGACGACGCCGCAGGCGGCGGAGAAGGAGGCGGTCTAGA

The SEQ ID NO.: 1 or a fragment or variant thereof may contained in a vector, for example, an expression vector adapted to be expressed in a subject. Vectors useful with the polynucleotides described herein include, for example, pIRES2-EGFP or pEF1alpha Myc/HIS.

The reporter compositions are functional under normal physiological conditions, comprising, for example, a pH from between about 6.8 to about 7.5; a pH from between about 6.9 to about 7.4; a pH from between about 7.0 to about 7.3; a pH from between about 7.1 to about 7.3; or a pH of 7. In certain conditions, the reporter composition is less functional or the function degrades, for example, under ischemic or apoptotic conditions.

In one aspect, the reporter compositions comprise proteins rich in amide protons. For example, LRPs and ARPs. The amide protons, for example, have a high exchange rate, e.g., from between about $100^{-1}$ s and about $700^{-1}$ s; from between about $450^{-1}$ s to about $650^{-1}$ s and/or from between about $490^{-1}$ s to about $600^{-1}$ s.

Reporter compositions according to one aspect may also comprising a polynucleotide encoding an LRP and/or an ARP. The polynucleotides may comprise the above described polypeptides. The polynucleotides may also comprise promoter and regulatory sequences or be contained in a vector, e.g., an expression vector. For example, expression vectors may comprise an IRES regulator. For example, exemplary vectors include, pIRES2-EGFP (available from Clontech) and/or pEF1alpha Myc/HIS (available from Invitrogen).

Kits are also provided herein. For example, a kit for MRI imaging comprise one or more of a vector expressing and LRP, a vector expressing and ARP, an LRP polypeptide, an APR polypeptide, and instructions for use. The kits may also provide means for administering the polypeptides or nucleotides, e.g., syringes. The kits may also provide buffers, pharmaceutically suitable carriers and the like. The instructions may provide information, for example, regarding storage, use, subject selection, administration, etc.

Figure 2:
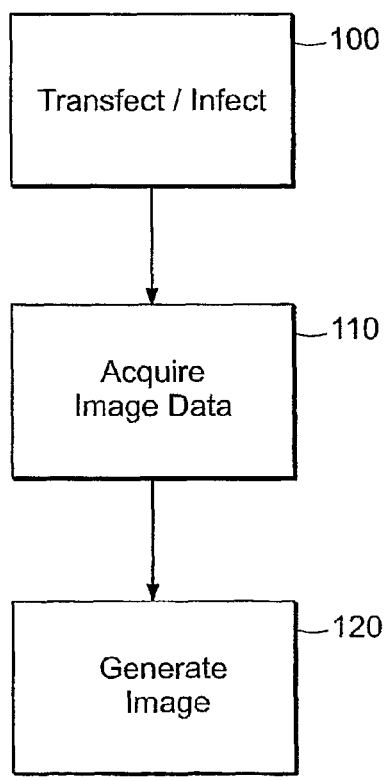
FIG. 2 is a high level flow diagram of an exemplary CEST based MR imaging using a MRI reporter gene of the present invention.

Referring now to the various figures of the drawing wherein like reference characters refer to like parts, there is shown in FIG. 2, a high level flow diagram generally illustrating an MR imaging process using the reporter genes and related methodology. It should be recognized that the following methodology is adaptable for use in a clinical or diagnostic settings such as diagnosing the extent of tumors and the biodistribution of gene therapy. The following is illustrative and should not be construed as limiting the use of the MRI reporter genes of the present invention to the below described process. It should be recognized that the following methodology does not include the process by which the MRI reporter gene is synthesized for the particular use, this is described further herein.

Initially, the MRI reporter gene is associated with the one or more cells to be imaged, such as by transfection or infection of the reporter gene, Step 100. For example, the reporter gene is introduced into the tissues of the area or region being imaged within a body or patient by injection and so as to be thereby transfect or infect the cells of interest in that area or region.

Thereafter, the object/body or a part of portion thereof is positioned or located within the MRI scanner so that the region or area of interest is appropriately located within the scanner and the magnetic fields being generated an the RF pulses being applied to the area/region of interest. For example, the body part is located so as to be generally located or positioned so as to be centrally located in the MR image.

Using a CEST based MR imaging technique, the area or region of interest is imaged and image data is acquired, Step 110. It is well within the skill of those in the art to adapt any of a number of MRI techniques known to those skilled in the art so as to be capable of carrying out a CEST based MR imaging. It should be recognized that the clinician or diagnostician can acquire plurality or multiplicity of image data that are spatially an/or temporal separated. For example, image data can be acquired on one day and another data acquisition be performed at another time (e.g., another day). In addition to the CEST based MRI imaging, further high resolution MRI imaging can be conducted as well. Such image data acquisition is generally included within this step of the process.

Following such data acquisition, the image data would be processed using any of a number of techniques known in the art, so as to for example generate an image for viewing by clinician or diagnostician. The image data acquired using the CEST MRI technique would be processed so as to delineate using the determined contrast, the location of the cells including the tissues including such cells, step 120. For example, the contrast is used to establish the location and size of a tumor within the body or is used to determine where genes administered for therapy have traveled to and/or the amount of such genes that have traveled to and accumulated within a given area.

A reporter gene according to the present invention is designed so as to maximize to the extent practicable the number of exchangeable protons per molecule. In this way, the concentration of the CEST can be minimized while maintaining measurable contrast. Such a reporter gene creates contrast material that is detectable in the micromolar range, be biodegradable by cells, distinguish viable from non-viable cells, and enable a constant endogenous level of expression even after cell division. Based on favorable in vitro (solution) results for CEST detection of amide protons in a poly-L-lysine (PPL), a reporter gene was designed encoding for a lysine rich protein (LRP) [Goffeney, N., Bulte, J. W., Duyn, J., Bryant, L. H., Jr. & van Zijl, P. C. Sensitive NMR detection of cationic-polymer-based gene delivery systems using saturation transfer via proton exchange. *J Am Chem Soc* 123, 8628-8629 (2001)].

Figure 3A:
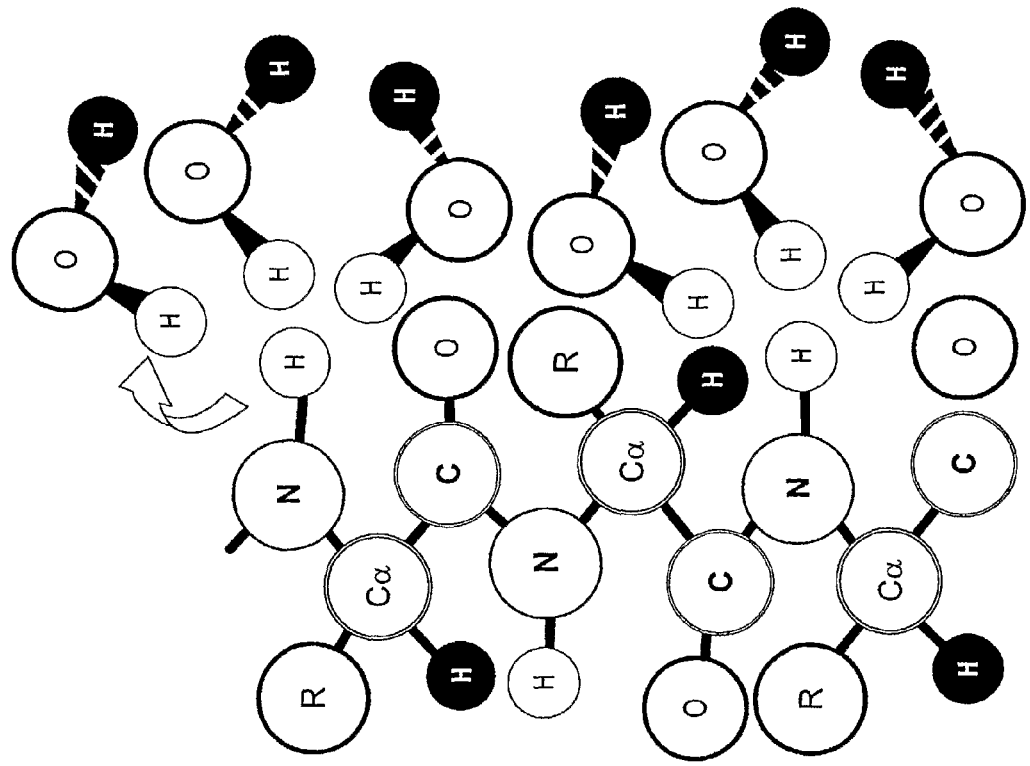
FIGS. 3A-D are various figures illustrating various aspects when LRP is used as an MR-CEST reporter.
Figure 3A:
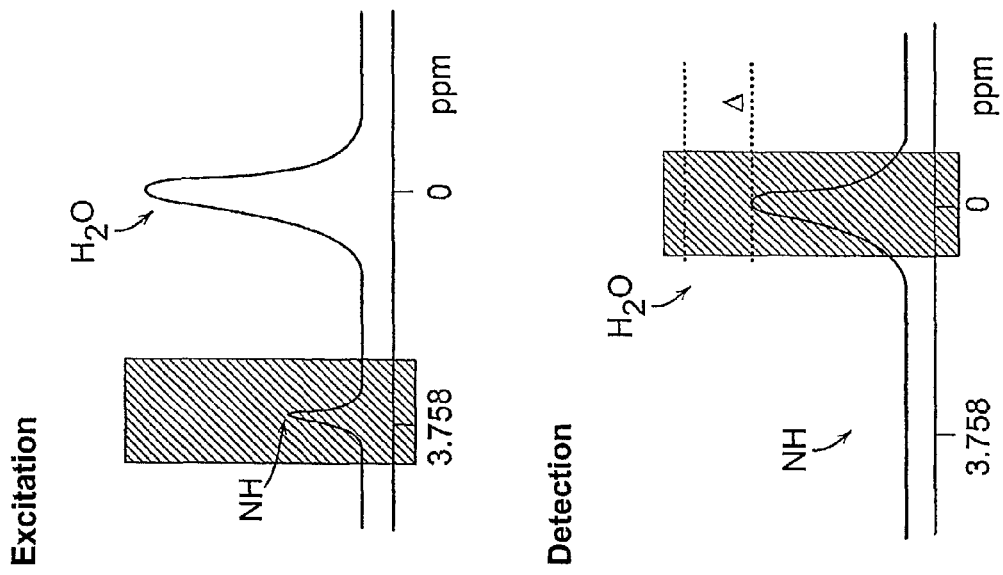
Figure 3C:
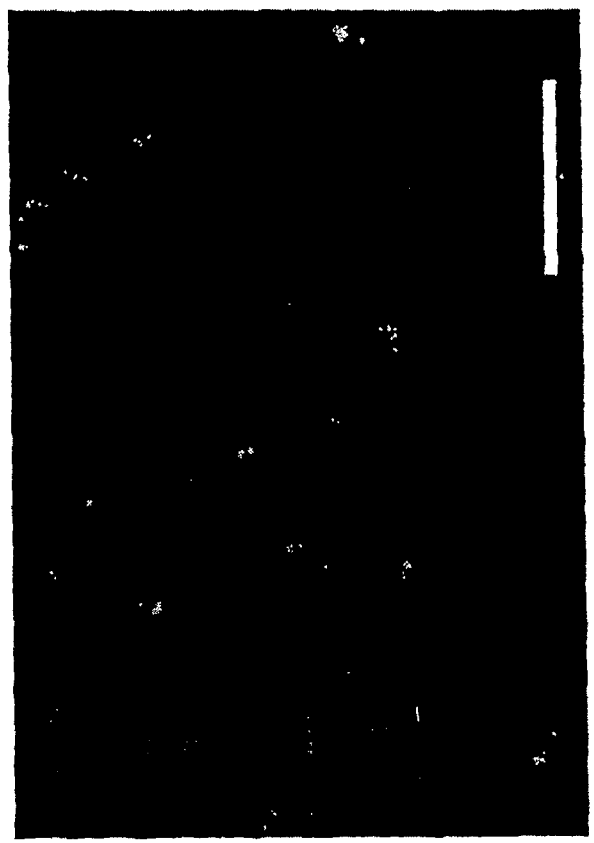
Figure 3B:
Figure 3D:
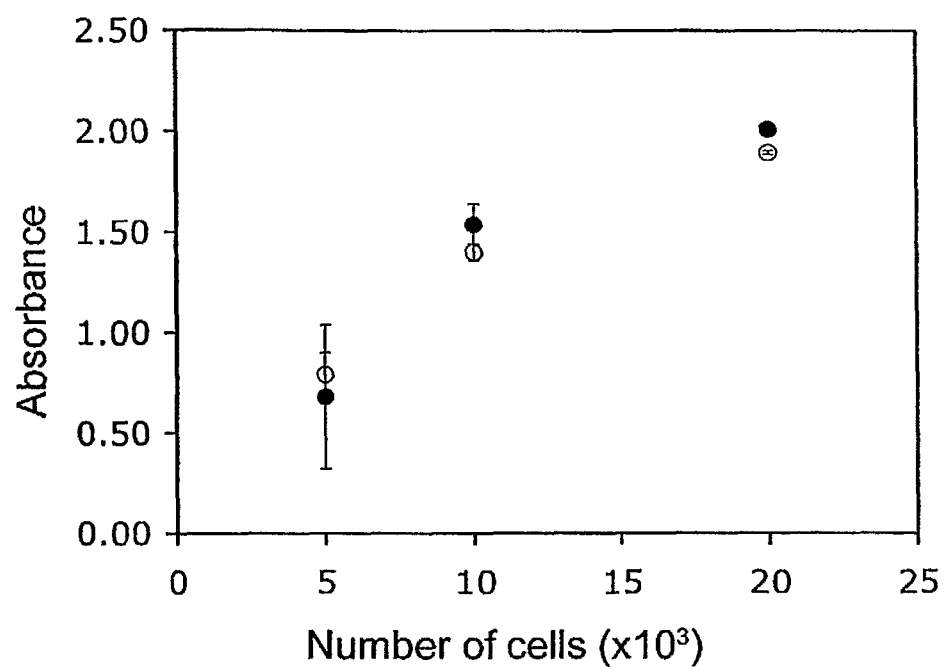

Eight synthetic oligonucleotides encoding for LRP were designed and cloned in tandem into a mammalian expression vector (total of 200 lysine residues; 32 kDa) co-expressing enhanced green fluorescent protein (EGFP) under an internal ribosome entry site (IRES) regulation. The vector was then transfected into the 9L rat glioma cell line. Control cells were transfected with an empty vector expressing only EGFP. After selection, two stable cell populations were established, namely cells expressing the artificial LRP and control cells. LRP expression was verified by immunofluorescence using a specific polyclonal antibody developed against the LRP. Both cell populations showed a weak non-specific staining around the nuclei, but LRP was observed only in the cytoplasm of the LRP expressing cells and not in control cells (FIGS. 3B,C). In order to monitor potential toxic side effects of LRP, the metabolic mitochondrial rate was measured using a MTS assay (FIG. 3D). No significant attenuation was observed for the growth and metabolic rate of LRP-expressing cells when compared to control cells.

Figure 4A:
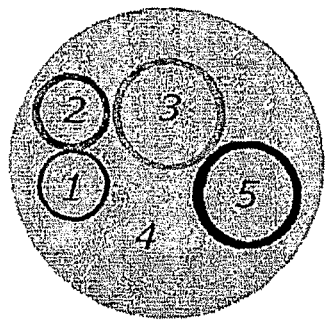
FIGS. 4A-D are various views relating to the CEST imaging of LRP cell extracts.
Figure 4B:
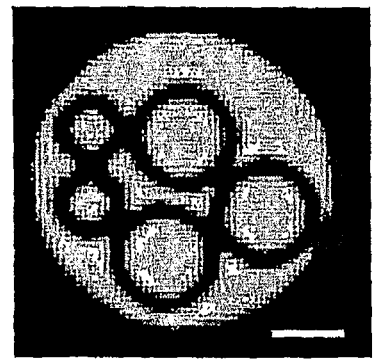
Figure 4C:
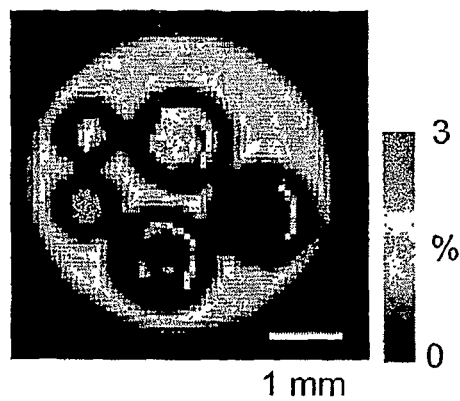
Figure 4D:
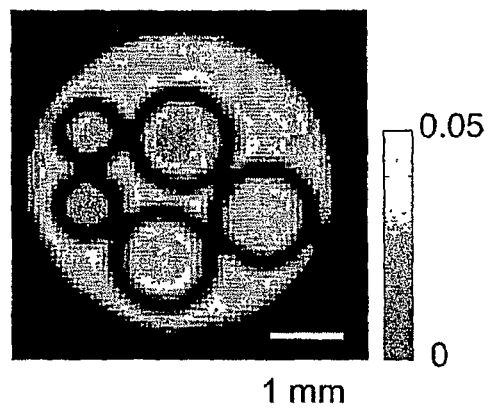

LRP potential as a reporter was first assessed in vitro (FIG. 4A). To remove potential contributions from processes other than selective saturation transfer from amide protons to water, the effect of RF irradiation at the amide proton frequency (+3.758 ppm from water) was compared with irradiating at −3.758 ppm from water. In the latter case, no MR contrast was observed (FIG. 4B), because no exchangeable protons resonate in the proton spectrum of our sample at this frequency. FIG. 4C shows a map of the difference in signal intensity (SI) between irradiating at these two frequencies, normalized by SI at the reference frequency. The protein extract from cells expressing LRP shows a significant SI rise above this background while the protein extract from control cells has a much lower, non-significant, effect (P>0.1). The average change in MR signal in extract from LRP expressing cells (0.87%, n=5) was significantly higher (t-test, 2-tailed, unpaired, P<0.05) than that of control cells (0.24%, n=4). Moreover, in pixel-by-pixel t-test maps (comparing the set of images saturated at $\Delta\omega=\pm3.758$ ppm), the pixels in the capillary containing the LRP extract show a significant change in MR signal, which is not detected in the control capillaries (FIG. 4D).

Figure 5A:
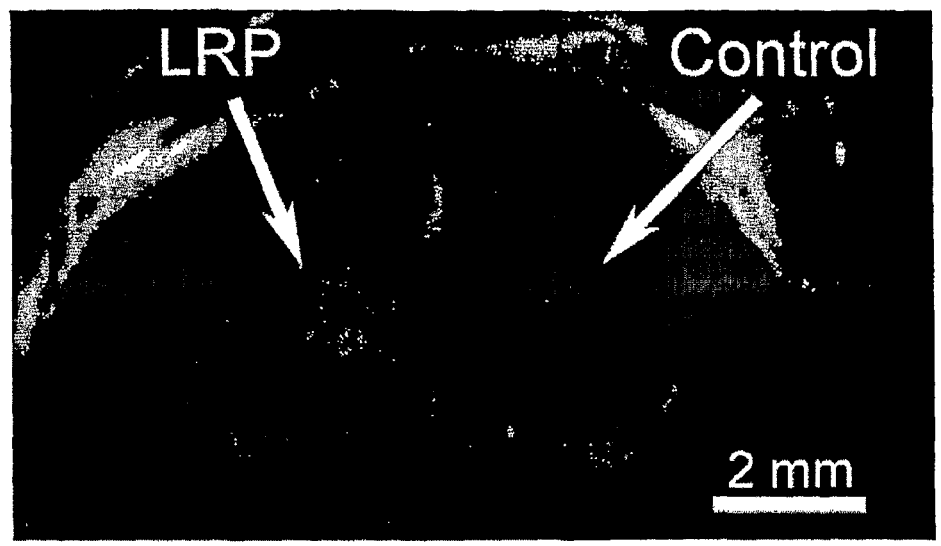
FIGS. 5 A-B are illustrations of an in vivo imaging of animals; where FIG. 5A includes anatomical images showing tumors expressing LRP (L) or EGPF (C, control) in two animals.
FIG. 5B us a illustration showing that an LRP-expressing tumor can be distinguished from control tumors in SI change map (overlaid on the a,c respectively, scale bar: 2 mm).
FIG. 5C is a graphical view showing mean change in SI (±SD) of LRP, control tumors, and normal brain regions (n=6, p=0.03, 2-tailed, unpaired t-test). In order to compare different mice, for each image the SI Change was normalized so the SI change of the brain will be zero. Proper adjustment of field homogeneity could only be done inside the brain, leading to some artifacts at the brain edge. It should be note that it is within skill of those knowledgeable in the art to correct such artifacts during post processing analysis.
Figure 5B:
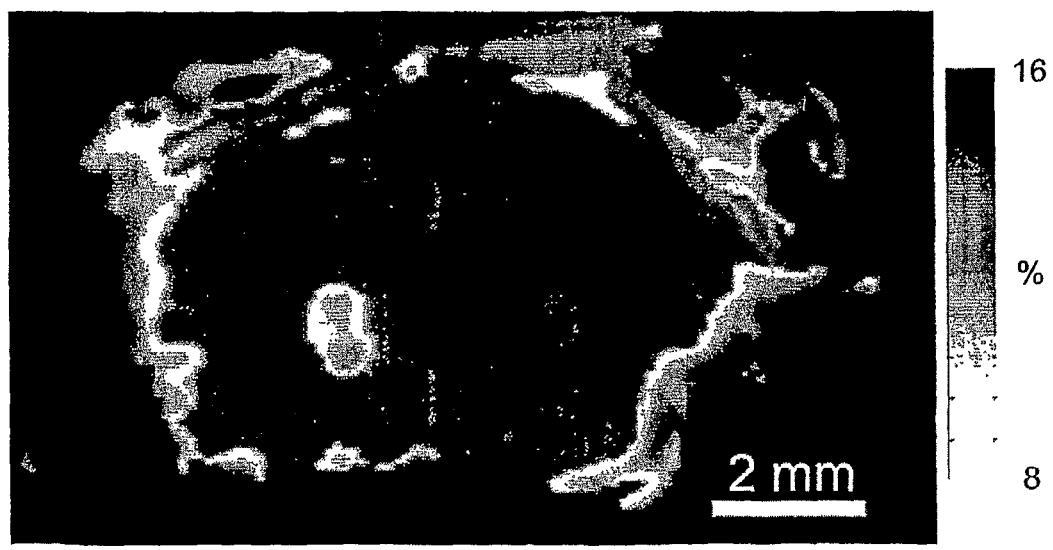
Figure 5C:
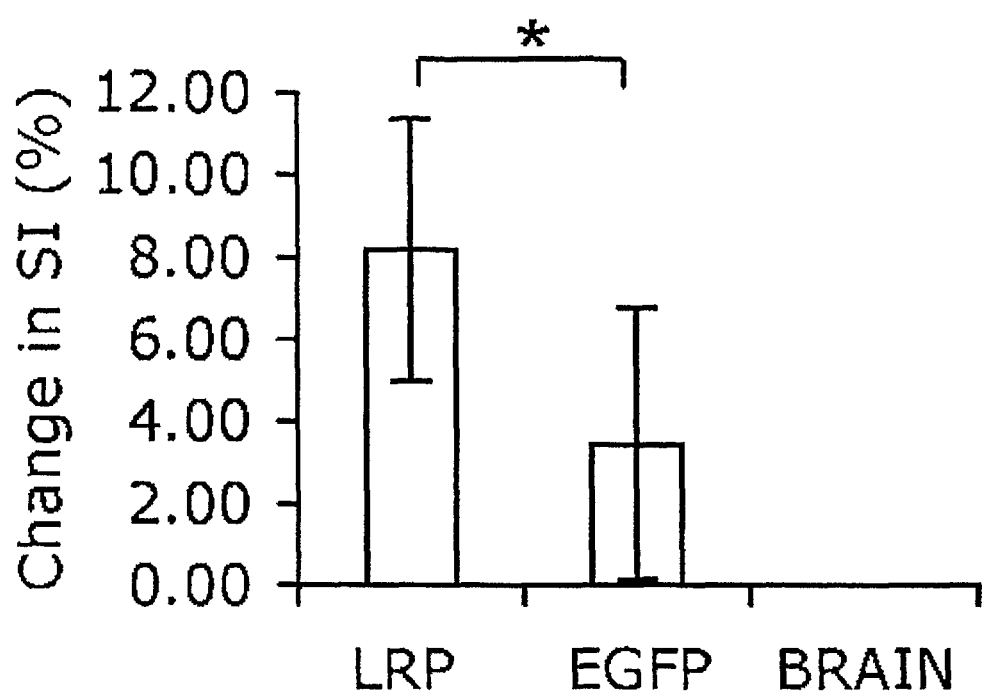

In order to evaluate the potential of the LRP as an MR reporter gene, LRP-expressing and a EGFP-expressing (control) tumors were inoculated in contralateral hemispheres of NOD-SCID mouse brains (n=6). In maps of the change in SI between irradiating at $\Delta\omega=\pm3.758$ ppm, the LRP expressing tumors could be differentiated from control tumors (FIG. 5). The average change in SI was 8.2% above the brain baseline for LRP tumors relative to 3.5% in the control tumors. This significant difference (6 mice, t-test, 2-tailed, unpaired, P=0.03) indicates that LRP can be used as a potential genetic reporter for tracking cells.

A variety of reporter genes are in use for fluorescence, bioluminesence, nuclear (PET, SPECT) and MR imaging. However, in most types of reporter genes, a gene with known activity is selected and given a new application, to report cellular activity or localization. These genes can be modified by genetic mutagenesis, as in the case of enhanced GFP or monomeric red fluorescent protein. When imaging of the reporter is based on enzymatic activity, chemical synthesis or modifications of the substrate can improve the contrast, as was described for imaging the herpes-simplex-virus-1 thymidine-kinase gene using PET, selecting for a specific *Renilla* Luciferase substrate for different bioluminescence imaging applications, or for MR imaging of the beta-galactosidase gene. In the present invention, the gene was designed de novo based on the desired properties (i.e., polypeptide with high exchange rate of the amide protons). Therefore, the lrp sequence is completely different from all other known genes, and so is its application.

In order to be practical, the signal produced by the reporter should be distinguishable from natural proteins expressed in cells. Recently, it was shown that endogenous proteins in brain [Zhou, J., Lal, B., Wilson, D. A., Laterra, J. & Van Zijl, P. C. Amide proton transfer (APT) contrast for imaging of brain tumors. *Magn Reson Med* 50, 1120-1126 (2003)] and tumor cells [Zhou, J., Payen, J. F., Wilson, D. A., Traystman, R. J. & van Zijl, P. C. Using the amide proton signals of intracellular proteins and peptides to detect pH effects in MRI. *Nat Med* 9, 1085-1090 (2003)] can be detected. For xenografted 9L glioma cells, the change in MR signal due to the amide proton transfer effects from these proteins occurred over a broad frequency range (2-4 ppm from the water peak). Thus, the CEST effect gained from LRP is more frequency selective than that of the total amide protons in the target cells and therefore distinguishable. In addition, CEST contrast is directly dependent on the number of selectively saturated protons exchanging with water protons and the exchange rate. Therefore, it is favorable when CEST reporter protons have a faster exchange rate than those in other proteins. Indeed, for 22 kDa PLL an exchange rate of 490 and 600 $s^{-1}$ was measured for the amide protons at pH=7.15 and pH=7.35 respectively (data not shown), in contrast to an exchange rate of 28 $s^{-1}$ previously measured in situ in the rat brain. The availability of MRI methods for measuring exchange rates of amide protons through the water signal, will allow determination of the presence of the contrast agent. Thus, specificity of both its frequency and exchange rate enables LRP to induce detectable MR contrast in vivo.

Another important feature of the LRP, since the base-catalyzed exchange of these protons is strongly pH dependent under physiological conditions (~factor of 10 reduction in rate per pH unit), is that the contrast will be lowered by an order of magnitude during ischemia or when cells die. Thus, the reporter gene of the present invention will be most effective under normal physiological conditions or in tumors where the intracellular pH ranges are 7.2-7.3 and 7-7.2, respectively. In addition, when cells die, the LRP molecules will no longer be produced, biologically degraded, and eventually disappear. This is in contrast to (super)paramagnetic agents, which can persist in dead cells for several weeks to months if not longer.

Although the foregoing describes an LRP as a CEST-based reporter gene, the present invention is not so-limited. It is within the scope of the present invention got additional frequency-specific reporter genes to be designed, for example to target imino, amine and guanidine protons, giving the potential of multiple labelling. Alternatively, MR double labelling in combination with existing (super)paramagnetic based reporters could be achieved.

Methods

Cloning of LRP: Two complimentary synthetic oligonucleotides (84 base pairs long) encoding the artificial LRP were designed so that after annealing they retain endonuclease restriction site overhangs corresponding to Bgl II at the 5'-end and BamH I at the 3'-end. The double-stranded LRP sequence was cloned into a bicistronic expression vector (pIRES2-EGFP, Clontech). After cloning, the new vector was digested with Bgl II and BamH I and the released insert was ligated into the Bgl II sites of the parental vector. This process was repeated twice, resulting in cloning of eight LRP sequences in tandem. The final insert encoding 200 lysine residues was verified by DNA sequencing.

Cell Culture and Transfections: Rat glioma (9L) cells were transfected with vector containing LRP or with empty vector using SuperFect® (QIAGEN)/Lipofectamine (Invitrogen) according to the manufacturer instructions. Stable cell populations were selected in cell culture media containing 0.6 mg/ml of G418.

Immunofluorescence: Cells were grown on glass chamber slides (Lab-Tek II, Nalge Nunc, USA) overnight, washed twice with PBS and once with cold acetone, then fixed with cold acetone for 10 min at −20° C. and air dried for 15 min. After overnight incubation at 4° C. with polyclonal antibody raised against the LRP (epitope: KKKKKKKKGSMKKKKKKKK (SEQ ID NO: 2), Proteintech, Il, USA) followed by 45 min incubation with anti-goat-Cy3 antibody (Molecular Probes) at room temperature, samples were mounted with antifade mounting medium containing DAPI (Vector laboratories, USA). Cells were analyzed using an epifluorescent microscope (OLYMPUS BX51).

Cell Proliferation Assay: Cells were dispensed in 96 well tissue culture plates at different cell densities (5,000 to 100,000 cells per well) in triplicate. After 48 hr incubation at 37° C. in a humidified 5% CO2 atmosphere, 20 µl/well MTS Reagent (Promega) was added, cells were incubated for 3 hrs, and the absorbance was recorded at 490 nm using a 96-well plate reader.

Cytoplasmic Protein Extraction: Proteins were extracted using M-PER® Mammalian Protein Extraction Reagent (PIERCE). Approximately $10^7$ cells where washed twice with PBS (on ice) and collected in a total volume of 20 ml of cold PBS. After centrifugation at 2500 g for 10 min at 4° C., the pellet was suspended in 1 ml of M-PER® and shaked gently for 10 min at 4° C. Cell debris was removed by centrifugating 15 min at 4° C. at 14000 g. The supernatant was transferred to a dialysis tube (cutoff: 3.5 kDa) and dialyzed twice against 10 mM PBS (pH=7.0, without Mg+/Ca+). A protease inhibitor cocktail was added (PIERCE; Halt™), and the protein extraction was stored at −80° C. Protein concentrations were determined using the Bradford assay (PIERCE).

MRI Phantom Preparation: Each phantom was constructed from 3 capillaries (1.2 inner diameter) each filled with approximately 50 µl cells extract or PBS (pH=7.0), and 2 capillaries (0.56 inner diameter) containing approximately 10 µl of 10 µM or 100 µM PLL (Sigma, pH=7.0, Mw=22-30 Kd). The capillaries were color-coded, sealed at the bottom and inserted in a 5 mm tube containing 300 µl of PBS (FIG. 4A).

Animal Experiments: All animal investigations were conducted in accordance with the Guiding Principles for the Care and Use of Research Animals. Intracranial 9L tumors were generated by sterotactic inoculation of $5 \times 10^4$ cells into the striatum of NOD-SCID male mice. In vivo MR imaging was performed 6 days after cell transplantation. Mice were anesthetized by isoflurane inhalation (1-2%) and immobilized in a vertical custom-made probe, equipped with a transmitter-receiver coil.

MR Parameters and Data Analysis: MR experiments were performed using a 11.7T Bruker spectrometer equipped with 5.0 mm and 25 mm imaging probes and a triple axis gradient high resolution NMR probe at 37° C. For mice anatomical imaging: RARE TR/TE=1000/10 ms. CEST imaging: spin echo sequences with TR/TE=9000/25 msec and TR/TE=9000/6.3 msec were used in vitro and in vivo, respectively. Eight images were acquired alternately with a saturation power of 1.64 µT for 4000 msec at $\Delta\omega \pm 3.758$ ppm from the water $^1$H frequency. Total acquisition time=38.4 min, FOV=5×5 mm for in vitro and 1.05−1.8×1.8 for in vivo with outer volume suppression, slice thickness=1 mm, and matrix=32×32 pixels.

MR data were analyzed using MATLAB 5.6.1 (MathWorks). Image were zero-filled to 64×64 and 128×128 matrix. Maps of change in SI were generated pixel by pixel from $[[SI^{-\Delta\omega} - SI^{+\Delta\omega}]/SI^{-\Delta\omega}] \times 100$, where $SI^{-\Delta\omega}$ and $SI^{+\Delta\omega}$ are the average SI of 4 images acquired with saturation at $\Delta\omega \pm 3.758$ ppm from the water $^1$H frequency, respectively. Pixel-by-pixel t-test maps were generated as described previously. Briefly, for each pixel, significance of the change in SI with saturation at $+\Delta\omega$ versus $-\Delta\omega$ was determined using a t-test (2 tails unpaired). The color-coded p-value maps were overlaid on spin echo images; non-significant changes ($p>0.05$) were discarded and clusters smaller than three pixels were removed. Signal to noise ratio; in vitro 175:1, in vivo 50:1. Pixels with signal intensity smaller than 50 or 18 times the SD of the noise were excluded from the in vitro and in vivo analysis, respectively. The exchange rate was measured using MR spectroscopy.

Although a preferred embodiment of the invention has been described using specific terms, such description is for illustrative purposes only, and it is to be understood that changes and variations may be made without departing from the spirit or scope of the following claims.

Incorporation By Reference

All patents, published patent applications and other references disclosed herein are hereby expressly incorporated by reference in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

---

The invention claimed is:

1. A magnetic resonance imaging system comprising:
an imaging apparatus configured to image one or more cells comprising a non-metallic reporter gene using a CEST magnetic resonance imaging (MRI) technique without binding of metallic or exogenous substrates or agents; wherein
the non-metallic reporter gene encodes a protein that is enriched with an amino acid from the list consisting of lysine, argentine, histidine, cysteine, tyrosine and serine and is used as a contrast agent.

2. The magnetic resonance imaging system of claim 1, further comprising a second non-metallic paramagnetic reporter gene, wherein the second non-paramagnetic reporter gene is different from the first non-paramagnetic reporter gene and encodes a lysine rich protein, an arginine rich protein, a histidine rich protein, cysteine rich protein, a tyrosine rich protein or a serine rich protein.

3. The magnetic resonance imaging system of claim 1, wherein the non-paramagnetic reporter gene encodes a lysine rich protein (LRP) and the contrast agent further comprises a therapeutically effective carrier.

4. The magnetic resonance imaging system of claim 3, wherein the LRP comprises from between about 50 to about 250 lysines.

5. The magnetic resonance imaging system of claim 3, wherein the LRP protein encoded by the reporter gene is functional under normal physiological conditions.

6. The magnetic resonance imaging system of claim 5, wherein normal physiological conditions comprise a pH from between about 6.8 to about 7.5.

7. The magnetic resonance imaging system of claim 3, wherein the LRP protein encoded by the reporter gene is not functional under ischemic or apoptotic conditions.

\* \* \* \* \*

UNITED STATES PATENT AND TRADEMARK OFFICE
CERTIFICATE OF CORRECTION

| | | |
|---|---|---|
| PATENT NO. | : 8,834,844 B2 | Page 1 of 1 |
| APPLICATION NO. | : 13/566785 | |
| DATED | : September 16, 2014 | |
| INVENTOR(S) | : Peter C. M. van Zijl et al. | |

It is certified that error appears in the above-identified patent and that said Letters Patent is hereby corrected as shown below:

IN THE CLAIMS:

Column 29, claim number 1, line number 32, "argentine" should read "arginine".

Signed and Sealed this
Twenty-third Day of June, 2015

Michelle K. Lee
*Director of the United States Patent and Trademark Office*